US006260556B1

(12) United States Patent
Legrand et al.

(10) Patent No.: US 6,260,556 B1
(45) Date of Patent: Jul. 17, 2001

(54) ANHYDROUS COMPOSITION FOR BLEACHING KERATIN FIBERS

(75) Inventors: Frédéric Legrand, Boulogne Billancourt; Jean Millequant, Saint Maur, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/492,778

(22) Filed: Jan. 28, 2000

(30) Foreign Application Priority Data

Jan. 29, 1999 (FR) .................................................. 99 01054

(51) Int. Cl.$^7$ .................................................. A61K 7/135
(52) U.S. Cl. .................................. 132/208; 8/101; 424/62
(58) Field of Search .............................. 132/208; 8/111, 8/101, 406; 424/62

(56) References Cited

U.S. PATENT DOCUMENTS

| | | |
|---|---|---|
| 2,261,002 | 10/1941 | Ritter . |
| 2,271,378 | 1/1942 | Searle . |
| 2,273,780 | 2/1942 | Dittmar . |
| 2,375,853 | 5/1945 | Kirby et al. . |
| 2,388,614 | 11/1945 | Kirby et al. . |
| 2,454,547 | 11/1948 | Bock et al. . |
| 2,528,378 | 10/1950 | Mannheimer . |
| 2,781,354 | 2/1957 | Mannheimer . |
| 2,961,347 | 11/1960 | Floyd . |
| 3,206,462 | 9/1965 | McCarty . |
| 3,227,615 | 1/1966 | Korden . |
| 3,589,578 | 6/1971 | Kamphausen . |
| 3,632,559 | 1/1972 | Matter et al. . |
| 3,836,537 | 9/1974 | Boerwinkle et al. . |
| 3,874,870 | 4/1975 | Green et al. . |
| 3,912,808 | 10/1975 | Sokol . |
| 3,915,921 | 10/1975 | Schlatzer, Jr. . |
| 3,917,817 | 11/1975 | Vanlerberghe et al. . |
| 3,929,990 | 12/1975 | Green et al. . |
| 3,966,904 | 6/1976 | Green et al. . |
| 4,001,432 | 1/1977 | Green et al. . |
| 4,005,193 | 1/1977 | Green et al. . |
| 4,013,787 | 3/1977 | Varlerberghe et al. . |
| 4,025,617 | 5/1977 | Green et al. . |
| 4,025,627 | 5/1977 | Green et al. . |
| 4,025,653 | 5/1977 | Green et al. . |
| 4,026,945 | 5/1977 | Green et al. . |
| 4,027,020 | 5/1977 | Green et al. . |
| 4,031,307 | 6/1977 | DeMartino et al. . |
| 4,131,576 | 12/1978 | Iovine et al. . |
| 4,165,367 | 8/1979 | Chakrabarti . |
| 4,170,637 | 10/1979 | Pum . |
| 4,172,887 | 10/1979 | Vanlerberghe et al. . |
| 4,189,468 | 2/1980 | Vanlerberghe et al. . |
| 4,197,865 | 4/1980 | Jacquet et al. . |
| 4,217,914 | 8/1980 | Jacquet et al. . |
| 4,240,450 | 12/1980 | Grollier et al. . |
| 4,349,532 | 9/1982 | Vanlerberghe et al. . |
| 4,390,689 | 6/1983 | Jacquet et al. . |
| 4,509,949 | 4/1985 | Huang et al. . |
| 4,591,610 | 5/1986 | Grollier . |
| 4,702,906 | 10/1987 | Jacquet et al. . |

(List continued on next page.)

FOREIGN PATENT DOCUMENTS

| | | |
|---|---|---|
| 38 14 356 | 9/1988 | (DE) . |
| 38 44 956 | 3/1996 | (DE) . |
| 197 23 538 | 9/1998 | (DE) . |
| 0 080 976 | 6/1983 | (EP) . |
| 0 122 324 | 10/1984 | (EP) . |
| 0 337 354 | 10/1989 | (EP) . |
| 0 557 203 | 8/1993 | (EP) . |
| 0 778 020 | 6/1997 | (EP) . |
| 0 827 738 | 3/1998 | (EP) . |
| 0 882 444 | 12/1998 | (EP) . |
| 1 400 366 | 12/1965 | (FR) . |
| 1 492 597 | 8/1967 | (FR) . |
| 1 583 363 | 10/1969 | (FR) . |
| 2 077 143 | 10/1971 | (FR) . |
| 2 080 759 | 11/1971 | (FR) . |
| 2 162 025 | 7/1973 | (FR) . |
| 2 190 406 | 2/1974 | (FR) . |
| 2 252 840 | 6/1975 | (FR) . |
| 2 270 846 | 12/1975 | (FR) . |
| 2 280 361 | 7/1976 | (FR) . |
| 2 316 271 | 1/1977 | (FR) . |
| 2 320 330 | 3/1977 | (FR) . |
| 2 336 434 | 7/1977 | (FR) . |
| 2 368 508 | 5/1978 | (FR) . |
| 2 383 660 | 10/1978 | (FR) . |
| 2 393 573 | 1/1979 | (FR) . |
| 2 413 907 | 8/1979 | (FR) . |
| 2 470 596 | 6/1981 | (FR) . |
| 2 505 348 | 11/1982 | (FR) . |
| 2 519 863 | 7/1983 | (FR) . |
| 2 542 997 | 9/1984 | (FR) . |
| 2 598 611 | 11/1987 | (FR) . |
| 2 751 533 | 1/1998 | (FR) . |
| 2 753 093 | 3/1998 | (FR) . |
| 2 753 094 | 3/1998 | (FR) . |
| WO 97/07776 | 3/1997 | (WO) . |

OTHER PUBLICATIONS

Richard J. Crawford et al., "A replacement for Rubine dye for detecting cationics on keratin", J. Soc. Cosmet Chem., vol. 31, No. 5, Sep./Oct. 1980, pp. 273–278.

M.R. Porter, "Handbook of Surfactants", Blackie & Son Ltd., Glasgow and London, 1991, pp. 116–178.

*Primary Examiner*—Todd E. Manahan
(74) *Attorney, Agent, or Firm*—Finnegan Henderson Farabow Garrett & Dunner, L.L.P.

(57) ABSTRACT

The present invention relates to anhydrous compositions for bleaching keratin fibers, in particular the hair, containing at least one alkaline agent, at least one peroxygenated salt, at least one anionic and/or nonionic amphiphilic polymer including at least one fatty chain, and at least one cationic or amphoteric substantive polymer, to the use of these compositions to prepare ready-to-use bleaching compositions by mixing with an aqueous hydrogen peroxide composition, and to a process for bleaching the hair using these anhydrous compositions.

47 Claims, No Drawings

U.S. PATENT DOCUMENTS

| | | |
|---|---|---|
| 4,719,282 | 1/1988 | Nadolsky et al. . |
| 4,761,273 | 8/1988 | Grollier et al. . |
| 4,839,166 | 6/1989 | Grollier et al. . |
| 4,996,059 | 2/1991 | Grollier et al. . |
| 5,089,252 | 2/1992 | Grollier et al. . |
| 5,783,175 * | 7/1998 | Schultz et al. ............................ 8/101 |
| 5,866,107 * | 2/1999 | Schultz ..................................... 8/101 |
| 5,888,484 | 3/1999 | Schmitt et al. . |
| 5,976,195 | 11/1999 | de la Mettrie et al. . |
| 5,989,295 | 11/1999 | de la Mettrie et al. . |
| 6,010,541 | 1/2000 | de la Mettrie et al. . |

* cited by examiner

ANHYDROUS COMPOSITION FOR BLEACHING KERATIN FIBERS

The present invention relates to anhydrous compositions for bleaching keratin fibers, in particular the hair, comprising a combination of at least one anionic amphiphilic polymer comprising at least one fatty chain, and/or at least one nonionic amphiphilic polymer comprising at least one fatty chain, and at least one cationic or amphoteric substantive polymer, to the use of these compositions for preparing ready-to-use bleaching compositions, to a process for bleaching keratin fibers using these compositions and to a packaging kit containing such a composition.

The bleaching of human keratin fibers, in particular the hair, is carried out by the oxidation of melanin, resulting in the dissolution and partial or total removal of this pigment.

Bleaching powders containing a peroxygenated reagent, such as ammonium or alkali metal persulphates, perborates or percarbonates, which are combined with an aqueous hydrogen peroxide composition at the time of use are generally used for bleaching the hair. Since peroxygenated salts and hydrogen peroxide are relatively stable in acidic medium, it is necessary to activate them at basic pH in order to obtain an adequate formation of oxygen. It is thus common to add alkaline compounds such as amines and alkaline silicates to bleaching powders.

This chemical treatment with oxidizing and alkaline agents is often very aggressive and modifies the chemical structure of keratin.

This is reflected in poor cosmetic properties of the hair, such as difficult disentangling, an unpleasant feel or coarse, dull hair, but especially in a degradation of the keratin fibers.

This degradation of the fibers is particularly undesirable since it irreversibly deteriorates the physicochemical properties of the hair. The hair becomes more porous and consequently more difficult to dry. It is more sensitive to various other hair treatments such as dyeing or permanent-waving, and its mechanical properties and surface properties are unfavorably modified, which is reflected, for example, by a reduction in the tractional or breaking strength or an increase in the coefficient of friction.

To overcome these drawbacks, use has been made hitherto of cationic or amphoteric substantive polymers. By applying these polymers to the hair, they improve its cosmetic properties, i.e., they make it softer, more shiny and easier to disentangle, but do not make it significantly possible to limit the degradation of keratin fibers.

The Inventors have discovered, surprisingly, that it is possible to significantly limit the degradation of keratin fibers by combining the cationic or amphoteric substantive polymer(s) usually used with one or more amphiphilic polymers comprising at least one fatty chain, which are also referred to as anionic and/or nonionic associative polymers.

Consequently, one subject of the present invention is an anhydrous composition for bleaching keratin fibers, in particular human keratin fibers, comprising, in a medium which is suitable for bleaching, at least one alkaline agent, at least one peroxygenated salt and, in addition, a combination of at least one anionic and/or nonionic amphiphilic polymer comprising at least one fatty chain, and at least one cationic or amphoteric substantive polymer.

A subject of the invention is also the use of such an anhydrous composition to prepare a ready-to-use bleaching composition.

A further subject of the invention is a process for bleaching keratin fibers using the anhydrous bleaching compositions above, as well as a packaging kit containing such a composition.

Other subjects of the invention will become apparent on reading the description and the examples which follow.

The anionic amphiphilic polymers comprising at least one fatty chain, which are used according to the present invention, in combination with cationic or amphoteric substantive polymers, are crosslinked or non-crosslinked copolymers comprising hydrophilic units derived from one or more monomers containing ethylenic unsaturation bearing a free carboxylic acid function, and hydrophobic units derived from one or more monomers containing ethylenic unsaturation bearing a hydrophobic side chain, and optionally crosslinking units derived from one or more polyunsaturated monomers.

The monomer(s) containing ethylenic unsaturation bearing a carboxylic acid function is(are) chosen from ethacrylic acid, methacrylic acid and acrylic acid, preferably from methacrylic acid and acrylic acid and mixtures thereof.

The monomer(s) containing ethylenic unsaturation bearing a hydrophobic side chain can be (i) fatty alkyl esters of unsaturated carboxylic acids, or (ii) allyl fatty alkyl ethers.

(i) The fatty alkyl esters of unsaturated carboxylic acids are chosen, for example, from ($C_{10}$–$C_{30}$), preferably ($C_{12}$–$C_{22}$), alkyl ethacrylates, methacrylates and/or acrylates.

They encompass, for example, lauryl acrylate, stearyl acrylate, decyl acrylate, isodecyl acrylate and dodecyl acrylate, as well as the corresponding methacrylates, i.e., lauryl methacrylate, stearyl methacrylate, decyl methacrylate, isodecyl methacrylate and dodecyl methacrylate.

(ii) The allyl fatty alkyl ethers forming the hydrophobic units of the anionic amphiphilic polymers of the present invention correspond to the formula $$CH_2=CR'CH_2—O—B_n—R \qquad (I)$$

in which:

R' is chosen from a hydrogen atom or a methyl group,

B is an ethylenoxy group, n is an integer ranging from 0 to 100,

R is a hydrocarbon-based group chosen from alkyl, arylalkyl, aryl, alkylaryl and cycloalkyl residues comprising from 8 to 30 carbon atoms, preferably from 10 to 24 carbon atoms, and more particularly from 12 to 18 carbon atoms.

One unit of formula (I), which is preferred according to the present invention, is a unit in which R' denotes a hydrogen atom, n is equal to 10 and R represents a stearyl ($C_{18}$) radical.

The crosslinking monomer is a compound comprising at least two non-conjugated polymerizable double bonds. Examples of which may include, but are not limited to, diallyl phthalate, allyl (meth)acrylate, divinylbenzene, (poly)ethylene glycol dimethacrylate, methylenebisacrylamide, polyallylsucrose or polyallylpentaerythritol.

Anionic amphiphilic polymers of the type described above are described, for example, in U.S. Pat. Nos. 3,915,921 and 4,509,949 (copolymers of (m)ethacrylic acid and of ($C_{10}$–$C_{30}$) alkyl (m)ethacrylates), or in patent EP-0 216 479 B2 (copolymers of (m)ethacrylic acid and of allyl fatty alcohol ethers), the disclosures of both of which are hereby incorporated by reference.

Examples of preferred polymers may include, but are not limited to:

crosslinked polymers of acrylic acid and of ($C_{10}$–$C_{30}$) alkyl acrylate, such as the polymers sold under the names PEMULEN TR1, PEMULEN TR2 and CARBOPOL 1382 by the company Goodrich, crosslinked polymers of acrylic acid and of ($C_{10}$–$C_{30}$) alkyl methacrylate, such as CARBOPOL ETD 2020 sold by the company Goodrich, the oxyethylenated methacrylic acid/ethyl acrylate/stearyl methacrylate (55/35/10) terpolymer, the oxyethylenated (25 EO) (meth)acrylic acid/ethyl acrylate/behenyl methacrylate terpolymer, and the crosslinked methacrylic acid/ethyl acrylate/steareth-10 allyl ether terpolymer.

The nonionic amphiphilic polymers comprising at least one fatty chain, which can be used according to the present invention, encompass, for example:

celluloses or hydroxyalkylcelluloses modified with groups comprising at least one fatty chain, such as an alkyl, arylalkyl or alkylaryl group containing an alkyl group which is preferably ($C_8$–$C_{22}$), such as the products NATROSOL PLUS GRADE 330 CS from the company Aqualon, BERMOCELL EHM 100 from the company Berol Nobel, or POLYSURF 67 from the company Hercules, or modified with polyalkoxylated alkylphenol groups, such as the product AMERCELL POLYMER HM-1500 from the company Amerchol;

hydroxypropyl guars modified with groups comprising at least one ($C_8$–$C_{22}$) fatty chain such as the products ESAFLOR HM 22 ($C_{22}$ alkyl chain) from the company Lamberti, or MIRACARE XC95-3 ($C_{14}$ alkyl chain) and RE205-1 ($C_{20}$ alkyl chain) from the company Rhône-Poulenc;

polyurethanes comprising at least one fatty chain of ($C_8$–$C_{30}$) alkyl or alkenyl type such as the product SER-AD FX 1100 from the company Servodelben, or the SMDI (saturated methylene diphenyl diisocyanate) polyethylene glycol(s) copolymer with a decyl end group;

the SMDI (saturated methylene diphenyl diisocyanate) polyethylene glycol(s) copolymer with an alkyl (methyl/$C_{18}$) end group, combined with a maltodextrin matrix, the HMDI (hexamethylene diisocyanate) diurethane of oxyethylenated (66 EO) and oxypropylenated (14 PO) $C_{10}$–$C_{18}$ alcohols, sold under the name ELFACOS T 212 by the company Akzo;

copolymers of vinylpyrrolidone and of hydrophobic monomers containing a fatty chain, such as the products ANTARON V216 or GANEX V216 (poly(vinylpyrrolidone/hexadecene)), ANTARON V220 or GANEX V220 (poly(vinylpyrrolidone/eicosene)) from the company ISP;

copolymers of ($C_1$–$C_6$) alkyl (meth)acrylates and of amphiphilic monomers comprising at least one fatty chain;

copolymers of hydrophilic (meth)acrylates and of hydrophobic monomers comprising at least one fatty chain, for example a poly(polyethylene glycol methacrylate/lauryl methacrylate).

Polyurethanes comprising at least one fatty chain of ($C_{10}$–$C_{20}$) alkyl type and hydroxyethylcelluloses modified with groups comprising at least one ($C_8$–$C_{22}$) alkyl group are preferred, in particular.

The anhydrous compositions contain the anionic and/or nonionic amphiphilic polymer(s) comprising at least one fatty chain in a proportion of from 0.03 to 30% by weight, preferably in a proportion of from 0.3 to 15% by weight.

In the bleaching compositions of the present invention, the anionic and/or nonionic amphiphilic polymer(s) comprising at least one fatty chain, which are described above, is(are) combined with at least one cationic or amphoteric substantive polymer.

In the cosmetics field, the term substantive polymer means a polymer capable, by virtue of its strong affinity for a support such as the hair, of forming a deposit thereon. The substantive nature is conventionally evaluated by means of the test described by Richard J. Crawford, *Journal of the Society of Cosmetic Chemists*, 1980, 31(5), pages 273–278, the disclosure of which is hereby incorporated by reference.

For the purposes of the present invention, the expression "cationic polymer" denotes any polymer containing cationic groups and/or groups that can be ionized into cationic groups.

The cationic polymers, which can be used in accordance with the present invention, can be chosen from any of those already known per se as improving the cosmetic properties of the hair, namely, in particular, those described in patent applications EP-A-337354 and EP-A-557203 and in French Patents FR-2 270 846, 2 383 660, 2 598 611, 2 470 596 and 2 519 863, the disclosures of all of which are hereby incorporated by reference.

The preferred cationic polymers are chosen from those which contain units comprising primary, secondary, tertiary and/or quaternary amine groups which can either form part of the main polymer chain or can be borne by a side substituent directly linked thereto.

The cationic polymers used generally have a number-average molecular mass from 500 to 5,000,000 approximately, and preferably from 1,000 to 3,000,000 approximately.

Among the cationic polymers which can be mentioned more particularly are polymers such as polyamine, polyamino amide and polyquaternary ammonium.

These are known products. They are described in particular in French Patent Nos. 2 505 348 or 2 542 997, the disclosures of both of which are hereby incorporated by reference. Among the said polymers which may be mentioned are:

(1) homopolymers or copolymers derived from acrylic or methacrylic esters or amides and comprising at least one of the units of formula (II), (III), (IV) or (V) below:

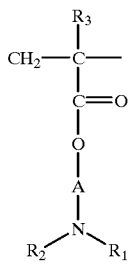

(II)

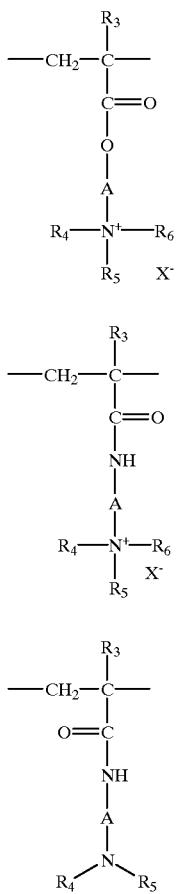

in which:
R₃, which may be identical or different, is chosen from a hydrogen atom or a CH₃ radical;
A, which may be identical or different, is chosen from a linear or branched alkyl group of 1 to 6 carbon atoms, preferably 2 or 3 carbon atoms, or a hydroxyalkyl group of 1 to 4 carbon atoms;
R₄, R₅ and R₆, which may be identical or different, are chosen from an alkyl group containing from 1 to 18 carbon atoms or a benzyl radical, and preferably an alkyl group containing from 1 to 6 carbon atoms;
R₁ and R₂, which may be identical or different, are chosen from hydrogen or an alkyl group containing from 1 to 6 carbon atoms, and preferably methyl or ethyl;
X is an anion derived from an inorganic or organic acid, such as a methosulphate anion or a halide such as chloride or bromide.

The polymers of the family (1) can also contain one or more units derived from comonomers which can be chosen from the family of acrylamides, methacrylamides, diacetone acrylamides, acrylamides and methacrylamides substituted on the nitrogen with lower ($C_1$–$C_4$) alkyls, acrylic or methacrylic acids or esters thereof, vinyllactams such as vinylpyrrolidone or vinylcaprolactam, and vinyl esters.

Thus, among these polymers of family (1) which may be mentioned are:

copolymers of acrylamide and of dimethylaminoethyl methacrylate quaternized with dimethyl sulphate or with a dimethyl halide, copolymers of acrylamide and of methacryloyloxyethyl trimethylammonium chloride described, for example, in patent application EP-A-080976, the disclosure of which is hereby incorporated by reference, the copolymer of acrylamide and of methacryloyloxyethyl trimethylammonium methosulphate, quaternized or non-quaternized vinylpyrrolidone/dialkylaminoalkyl acrylate or methacrylate copolymers. These polymers are described in detail in French Patents 2 077 143 and 2 393 573, the disclosures of both of which are hereby incorporated by reference, dimethylaminoethyl methacrylate/vinylcaprolactam/vinylpyrrolidone terpolymers, vinylpyrrolidone/methacrylamidopropyldimethylamine copolymers, and quaternized vinylpyrrolidone/dimethylaminopropylmethacrylamide copolymers.

(2) The cellulose ether derivatives containing quaternary ammonium groups, described in French patent 1,492,597, the disclosure of which is hereby incorporated by reference. These polymers are also defined in the CTFA dictionary as quaternary ammoniums of hydroxyethylcellulose which has reacted with an epoxide substituted with a trimethylammonium group.

(3) Cationic cellulose derivatives such as cellulose copolymers or cellulose derivatives grafted with a water-soluble monomer of quaternary ammonium, and described in particular in U.S. Pat. No. 4,131,576, the disclosure of which is hereby incorporated by reference, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

(4) The cationic polysaccharides described more particularly in U.S. Pat. Nos. 3,589,578 and 4,031,307, the disclosures of both of which are hereby incorporated by reference, such as guar gums containing cationic trialkylammonium groups. Guar gums modified with a salt (e.g., chloride) of 2,3-epoxypropyltrimethylammonium are used, for example.

(5) Polymers comprising piperazinyl units and of divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, in particular, in French patents 2,162,025 and 2,280,361, the disclosures of which are hereby incorporated by reference.

(6) Water-soluble polyamino amides prepared in particular by polycondensation of an acidic compound with a polyamine. These polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative. The crosslinking agent is used in proportions ranging from 0.025 to 0.35 mol per amine group of the polyamino amide. These polyamino amides can be alkylated or, if they contain one or more tertiary amine functions, they can be quaternized. Such polymers are described, in particular, in French patents 2,252,840 and 2,368,508, the disclosures of both of which are hereby incorporated by reference.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are described in particular in French patent 1,583,363, the disclosure of which is hereby incorporated by reference.

Among these derivatives, mention may be made more particularly of the adipic acid/dimethylaminohydroxypropyl/diethylenetriamine polymers sold under the name CARTARETINE F, F4 or F8 by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is from 0.8:1 to 1.4:1. The polyamino amide resulting therefrom is reacted with epichlorohydrin in a molar ratio of epichlorohydrin relative to the secondary amine group of the polyamino amide of from 0.5:1 to 1.8:1. Such polymers are described in particular in U.S. Pat. Nos. 3,227,615 and 2,961,347, the disclosures of both of which are hereby incorporated by reference.

(9) Cyclopolymers of alkyldiallylamine or of dialkyldiallylammonium, such as the homopolymers or copolymers containing, as main constituent of the chain, units corresponding to formula (VI) or (VII):

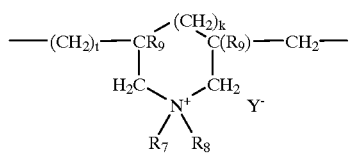

(IV)

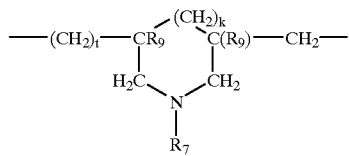

(VII)

in which:
formulae k and t are equal to 0 or 1, the sum k+t being equal to 1;
$R_9$ is chosen from a hydrogen atom or a methyl radical;
$R_7$ and $R_8$, independently of each other, are chosen from an alkyl group having from 1 to 22 carbon atoms, a hydroxyalkyl group in which the alkyl group preferably has 1 to 5 carbon atoms, or a lower ($C_1$–$C_4$) amidoalkyl group, or $R_7$ and $R_8$ can denote, together with the nitrogen atom to which they are attached, heterocyclic groups such as piperidyl or morpholinyl;
$Y^-$ is an anion such as bromide, chloride, acetate, borate, citrate, tartrate, bisulphate, bisulphite, sulphate or phosphate. These polymers are described in particular in French patent 2,080,759 and in its Certificate of Addition 2,190,406, the disclosures of which are hereby incorporated by reference.

(10) The quaternary diammonium polymer containing repeating units corresponding to the formula:

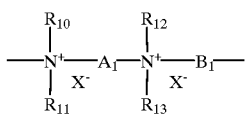

(VIII)

in which:
$R_{10}$, $R_{11}$, $R_{12}$ and $R_{13}$, which may be identical or different, are chosen from aliphatic, alicyclic or arylaliphatic radicals containing from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second heteroatom other than nitrogen, or alternatively $R_{10}$, $R_{11}$, $R_{12}$ and $R_{13}$ represent a linear or branched ($C_1$–$C_6$) alkyl radical substituted with a nitrile, ester, acyl or amide group or a group —CO—O—$R_{14}$—D or —CO—NH—$R_{14}$—D where $R_{14}$ is an alkylene and D is a quaternary ammonium group;
$A_1$ and $B_1$ are chosen from polymethylene groups containing from 2 to 20 carbon atoms which may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and
is an anion derived from an inorganic or organic acid;
$A_1$, $R_{10}$ and $R_{12}$ can form, with the two nitrogen atoms to which they are attached, a piperazine ring. In addition, if $A_1$ denotes a linear or branched, saturated or unsaturated alkylene or hydroxyalkylene radical, $B_1$ can also denote a group —$(CH_2)_n$—CO—D—OC—$(CH_2)_n$—
in which:
n is an integer ranging from 1 to 100 and preferably 1 to 50,
D is chosen from:
a) a glycol residue of formula:
—O—Z—O—, where Z is chosen from a linear or branched hydrocarbon radical or a group corresponding to one of the following formulae:

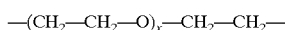
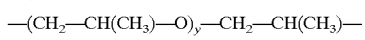

where x and y are each an integer from 1 to 4, representing a defined and unique degree of polymerization or any number from 1 to 4 representing an average degree of polymerization;
b) a bis-secondary diamine residue such as a piperazine derivative;
c) a bis-primary diamine residue of formula: —NH—Y—NH—, where Y is chosen from a linear or branched hydrocarbon radical, or alternatively the divalent radical

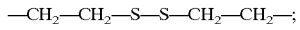

d) a ureylene group of formula: —NH—CO—NH—.
Preferably, $X^-$ is an anion such as chloride or bromide.
These polymers generally have a number-average molecular mass ranging from 1,000 to 100,000.

Polymers of this type are described, in particular, in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, the disclosures of all of which are hereby incorporated by reference.

Polymers which can be used more particularly are those comprising repeating units corresponding to formula (IX) below:

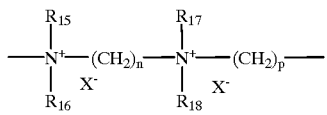

(IX)

in which:

$R_{15}$, $R_{16}$, $R_{17}$ and $R_{18}$, which may be identical or different, are chosen from an alkyl or hydroxyalkyl radical containing from 1 to 4 carbon atoms approximately;

n and p are integers ranging from 2 to 20 approximately; and

X$^-$ is an anion derived from an inorganic or organic acid.

(11) Polyquaternary ammonium polymers comprising units of formula (X):

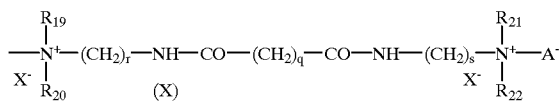

in which formula:

$R_{19}$, $R_{20}$, $R_{21}$ and $R_{22}$, which may be identical or different, are chosen from a hydrogen atom or a methyl, ethyl, propyl, β-hydroxyethyl, β-hydroxypropyl or —CH$_2$CH$_2$(OCH$_2$CH$_2$)$_p$OH radical, where p is equal to 0 or to an integer ranging from 1 to 6, with the proviso that $R_{19}$, $R_{20}$, $R_{21}$ and $R_{22}$ do not simultaneously represent a hydrogen atom, r and s, which may be identical or different, are integers ranging from 1 to 6, q is equal to 0 or to an integer ranging from 1 to 34, X is a halogen atom, A is chosen from a dihalide radical or preferably represents —CH$_2$—CH$_2$—O—CH$_2$—CH$_2$—.

Such compounds are described in particular in patent application EP-A-122,324, the disclosure of which is hereby incorporated by reference.

(12) Quaternary polymers of vinylpyrrolidone and of vinylimidazole.

(13) Polyamines such as the product referred to under the name Polyethylene glycol (15) tallow polyamine in the CTFA dictionary.

(14) Crosslinked polymers of methacryloyloxy (C$_1$–C$_4$) alkyltri(C$_1$–C$_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with a compound containing olefinic unsaturation, in particular methylenebisacrylamide. It is more particularly possible to use an acrylamide/methacryloyloxyethyl trimethylammonium chloride (20/80 by weight) crosslinked copolymer in the form of a dispersion containing 50% by weight of the said copolymer in mineral oil. This dispersion is sold under the name SALCARE® SC 92 by the company Allied Colloids. It is also possible to use a crosslinked homopolymer of methacryloyloxyethyl trimethylammonium chloride containing about 50% by weight of the homopolymer in mineral oil or in a liquid ester. These dispersions are sold under the names SALCARE® SC 95 and SALCARE® SC 96 by the company Allied Colloids. The methosulphate of the copolymer of methacryloyloxyethyl trimethylammonium and of methacryloyloxyethyldimethylacetylammonium, sold under the name PLEX7525L by the company Rohm GmbH (CTFA name: Polyquaternium-35), can also be used.

Other cationic polymers, which can be used in the context of the invention, are polyalkyleneimines, in particular polyethyleneimines, polymers containing vinylpyridine or vinylpyridinium units, condensates of polyamines and epichlorohydrin, polyquaternary ureylenes and chitin derivatives.

The amphoteric polymers, which can be used in accordance with the present invention, can be chosen from polymers containing units K and M distributed randomly in the polymer chain, in which K is chosen from a unit derived from a monomer containing at least one basic nitrogen atom and M is chosen from a unit derived from an acid monomer containing one or more carboxylic or sulphonic groups, or alternatively K and M can be chosen from groups derived from carboxybetaine or sulphobetaine zwitterionic monomers;

K and M can also be chosen from a cationic polymer chain containing primary, secondary, tertiary or quaternary amine groups, in which at least one of the amine groups bears a carboxylic or sulphonic group connected via a hydrocarbon radical or alternatively K and M form part of a chain of a polymer containing an α,β-dicarboxylic ethylene unit in which one of the carboxylic groups has been made to react with a polyamine containing one or more primary or secondary amine groups.

The amphoteric film-forming polymers corresponding to the definition given above which are more particularly preferred are chosen from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylates and acrylates, dialkylaminoalkylmethacrylamides and -acrylamides. Such compounds are described in U.S. Pat. No. 3,836,537, the disclosure of which is hereby incorporated by reference. Mention may also be made of the sodium acrylate/acrylamidopropyltrimethylammonium chloride copolymer.

The vinyl compound can also be a dialkyldiallylammonium salt such as diethyldiallylammonium chloride.

(2) polymers containing units derived from:
   a) at least one monomer chosen from acrylamides and methacrylamides substituted on the nitrogen with an alkyl radical,
   b) at least one acidic comonomer containing one or more reactive carboxylic groups, and
   c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides, which are more particularly preferred according to the invention, are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991), the disclosure of which is hereby incorporated by reference, name is octylacrylamide/acrylates/butylaminoethyl methacrylate copolymer are particularly used.

(3) crosslinked and alkylated polyamino amides partially or totally derived from polyamino amides of general formula:

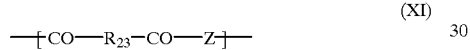

(XI)

in which:

$R_{23}$ is chosen from a divalent radical derived from a saturated dicarboxylic acid, a mono- or dicarboxylic aliphatic acid containing an ethylenic double bond, an ester of a lower alkanol, having from 1 to 6 carbon atoms, of these acids or a radical derived from the addition of any one of the acids to a bis(primary) or bis(secondary) amine, and Z is chosen from a bis(primary), mono- or bis(secondary) polyalkylene-polyamine radical and preferably represents:

a) in proportions of from 60 to 100 mol %, the radical

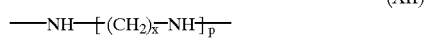

(XII)

where x=2 and p=2 or 3, or alternatively x=3 and p=2,
this radical being derived from diethylenetriamine, from triethylenetetraamine or from dipropylenetriamine;

b) in proportions of from 0 to 40 mol %, the radical (XII) above in which x=2 and p=1 and which is derived from ethylenediamine, or the radical derived from piperazine:

c) in proportions of from 0 to 20 mol %, the —NH—$(CH_2)_6$—NH— radical derived from hexamethylenediamine. These polyamino amines being crosslinked by addition of a difunctional crosslinking agent chosen from epihalohydrines, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having from 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid.

The alkane sultones used in the alkylation are preferably propane sultone or butane sultone, the salts of the alkylating agents are preferably the sodium or potassium salts.

(4) polymers containing zwitterionic units of formula:

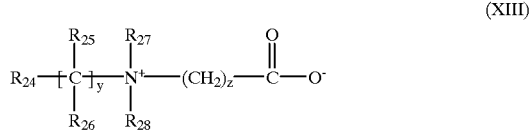

(XIII)

in which:

$R_{24}$ is chosen from a polymerizable unsaturated group such as an acrylate, methacrylate, acrylamide or methacrylamide group;

y and z is chosen from an integer from 1 to 3;

$R_{25}$ and $R_{26}$ are chosen from a hydrogen atom, and methyl, ethyl and propyl radicals;

$R_{27}$ and $R_{28}$ are chosen from a hydrogen atom or an alkyl radical such that the sum of the carbon atoms in $R_{27}$ and $R_{28}$ does not exceed 10.

The polymers comprising such units can also contain units derived from non-zwitterionic monomers such as dimethyl- or diethylaminoethyl acrylate or methacrylate or alkyl acrylates or methacrylates, acrylamides or methacrylamides or vinyl acetate.

By way of example, mention may be made of the copolymer of methyl methacrylate/dimethyl carboxymethylammonio methyl ethylmethacrylate.

(5) polymers derived from chitosan containing monomer units corresponding to formulae (XIV), (XV) and (XVI) below:

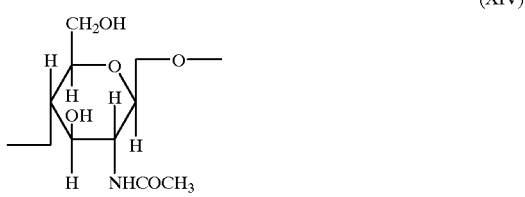

(XIV)

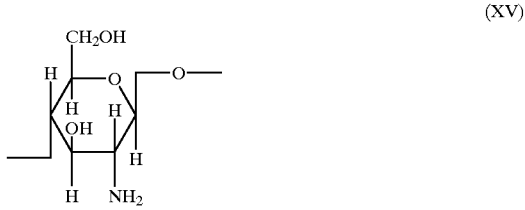

(XV)

-continued

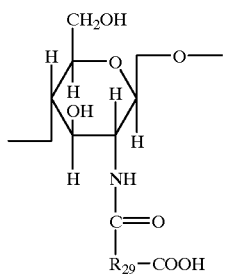
(XVI)

the unit (XIV) being present in proportions ranging from 0 to 30%, the unit (XV) in proportions of from 5 to 50% and the unit (XVI) in proportions of from 30 to 90%, it being understood that, in unit (XVI), $R_{29}$ represents a radical of formula:

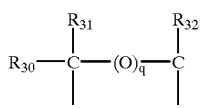
(XVII)

in which:
if q=0, $R_{30}$, $R_{31}$, and $R_{32}$, which may be identical or different, each are chosen from a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulphonic groups, an alkylthio residue in which the alkyl group bears an amino residue, at least one of the radicals $R_{30}$, $R_{31}$ and $R_{32}$ being, in this case, a hydrogen atom;
or, if q=1, $R_{30}$, $R_{31}$ and $R_{32}$ each represent a hydrogen atom, as well as the salts formed by these compounds with bases or acids.
(6) polymers derived from the N-carboxyalkylation of chitosan, such as N-carboxymethylchitosan or N-carboxybutylchitosan.
(7) polymers corresponding to the general formula (XVIII) as are described, for example, in French patent 1,400,366, the disclosure of which is hereby incorporated by reference:

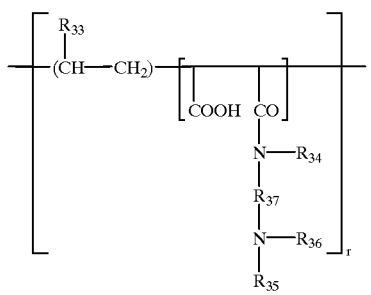
(XVIII)

in which:
r is such that the molecular mass of the final polymer is from 500 to 5,000,000, and preferably from 1,000 to 3,000,000.

$R_{33}$ is chosen from a hydrogen atom, a $CH_3O$, $CH_3CH_2O$ or phenyl radical;
$R_{34}$ is chosen from a hydrogen or a lower alkyl radical such as methyl or ethyl;
$R_{35}$ is chosen from hydrogen or a lower alkyl radical such as methyl or ethyl;
$R_{36}$ is chosen from a lower alkyl radical such as methyl or ethyl or a radical corresponding to the formula:

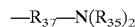

($R_{35}$ having the meanings mentioned above);
$R_{37}$ is chosen from a $—CH_2—CH_2—$, $—CH_2—CH_2—CH_2—$ or $—CH_2—CH(CH_3)—$ group as well as the higher homologues of these radicals and containing up to 6 carbon atoms.
(8) amphoteric polymers of the type —D—X—D—X chosen from:
a) polymers obtained by the action of chloroacetic acid or sodium chloroacetate on compounds containing at least one unit of formula:

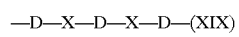

where D denotes a radical

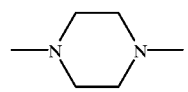

and X denotes the symbol E or E', E or E', which may be identical or different, is chosen from a divalent radical which is an alkylene radical containing a straight or branched chain containing up to 7 carbon atoms in the main chain, which is unsubstituted or substituted with hydroxyl groups and which can contain, in addition to the oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups;
b) polymers of formula:

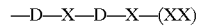

in which D denotes a radical

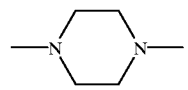

and X denotes the symbol E or E' and at least once E'; E having the meaning given above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) (C₁–C₅)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

The cationic or amphoteric substantive polymers can also bear hydrophobic groups.

They are chosen, for example, from cellulose derivatives containing quaternary ammonium groups and polyacrylates containing amino side groups, such as, for example:

celluloses containing quaternary ammonium groups, modified with groups comprising at least one fatty chain, chosen from alkyl, arylalkyl and alkylaryl groups comprising at least 8 carbon atoms, or mixtures thereof, hydroxyethylcelluloses containing quaternary ammonium groups modified with groups comprising at least one fatty chain, chosen from alkyl, arylalkyl and alkylaryl groups comprising at least 8 carbon atoms, or mixtures thereof, polyacrylates containing amino side groups, which may or may not be quaternized, possessing hydrophobic groups.

The alkyl radicals borne by the above celluloses or hydroxyethylcelluloses containing quaternary ammonium groups preferably comprise from 8 to 30 carbon atoms.

The aryl radicals preferably are chosen from phenyl, benzyl, naphthyl or anthryl groups.

Among the cationic or amphoteric substantive polymers which can be used according to the invention, those which are preferred in particular are:

the dimethyldiallylammonium chloride homopolymer sold under the name MERQUAT 100 DRY by the company Merck;

the copolymers of dimethyldiallylammonium chloride and of acrylamide sold under the name MERQUAT 2200 by the company Calgon;

the polymers of poly(quaternary ammonium) type prepared and described in French patent 2 270 846, the disclosure of which is hereby incorporated by reference, comprising repeating units corresponding to formula (XXI) below:

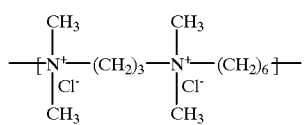

(XXI)

and in particular those whose weight-average molar mass, determined by gel permeation chromatography, ranges from 9500 to 9900;

the polymers of poly(quaternary ammonium) type prepared and described in French patent 2 270 846, the disclosure of which is hereby incorporated by reference, comprising repeating units corresponding to the formula (XXII) below:

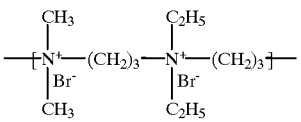

(XXII)

and in particular those whose weight-average molar mass, determined by gel permeation chromatography, is about 1200;

the polymers of poly(quaternary ammonium) type described in U.S. Pat. Nos. 4,390,689, 4,702,906 and 4,719,282, the disclosures of all of which are hereby incorporated by reference, and comprising repeating units corresponding to formula (XXIII) below:

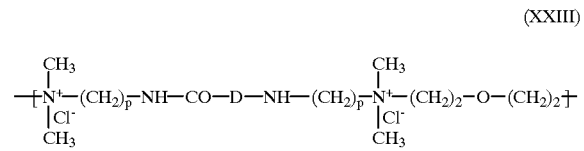

(XXIII)

in which:

p is an integer ranging from 1 to 6,

D is chosen from a single bond or a group —(CH₂)ᵣ—CO— in which r is 4 or 7, and in particular those whose weight-average molar mass is less than 100,000, preferably less than or equal to 50,000;

the following amphoteric copolymers:

the diallyldimethylammonium chloride/acrylic acid (80/20) copolymer sold under the name MERQUAT 280 DRY by the company Calgon (CTFA name: Polyquaternium-22);

the dimethyldiallylammonium chloride/acrylic acid (95/5) copolymer sold under the name MERQUAT 295 DRY by the company Calgon (CTFA name: Polyquaternium-22);

the copolymer of methacrylamidopropyltrimonium chloride, of acrylic acid and or methyl acrylate, sold under the name MERQUAT 2001 by the company Calgon (CTFA name: Polyquaternium-47); and the acrylamide/dimethyldiallylammonium chloride/acrylic acid terpolymer sold under the name MERQUAT PLUS 3330 DRY by the company Calgon (CTFA name: Polyquaternium-39).

In the above list of substantive polymers, the amphoteric copolymers Polyquaternium-22, Polyquaternium-39 and Polyquaternium-47 (CTFA names) are preferred most particularly.

The anhydrous bleaching compositions contain the cationic or amphoteric substantive polymer in a proportion of from 0.03 to 30% by weight, preferably in a proportion of from 0.3 to 15% by weight, relative to the anhydrous composition.

The weight ratio of the anionic and/or nonionic amphiphilic polymer(s) to the cationic or amphoteric substantive polymer ranges generally from 10:1 to 1:10 and preferably from 5:1 to 1:5.

As indicated above, the anhydrous bleaching composition contains at least one alkaline agent and at least one peroxygenated salt.

The alkaline agent is chosen from ammonium salts such as ammonium chloride, sulphate, phosphate or nitrate, alkali metal or alkaline-earth metal silicates, phosphates or carbonates, in particular alkali metal metasilicates.

The peroxygenated salts are chosen from ammonium or alkali metal persulphates, percarbonates and perborates.

Persulphates are preferably used and, among these, mainly sodium persulphate and potassium persulphate.

The compositions of the invention contain from 20 to 70% by weight, and preferably from 30 to 60% by weight, of peroxygenated salt relative to the total weight of the anhydrous composition.

The bleaching compositions according to the present invention can also contain adjuvants of any kind usually used in bleaching compositions, which are capable of facilitating the handling and application, of improving the storage or efficacy of the compositions and of improving the cosmetic properties of the treated hair.

These adjuvants are, for example, agents for controlling the release of oxygen, such as magnesium carbonate and magnesium oxide, water-soluble thickening or gelling polymers such as celluloses and derivatives thereof, for instance hydroxyethylcellulose, hydroxypropylcellulose and hydroxypropylmethylcellulose, starch and starch derivatives, hydroxypropyl guar and guar gum, alginates, polysaccharides, polyvinylpyrrolidone, carboxymethylcellulose, xanthan gum, gum arabic, gatti gum, gum tragacanth, polyacrylamides and poly(acrylic acids), anionic, nonionic, cationic, amphoteric or zwitterionic surfactants and mixtures thereof, mineral or plant oils, waxes, granulation adjuvants, binders, mineral fillers such as silica and clay, opacifiers such as titanium oxide, dyes, sequestering agents and fragrances.

Needless to say, a person skilled in the art will take care to select this or these optional additional compound(s) and the amount thereof, such that the advantageous properties intrinsically associated with the bleaching composition in accordance with the invention are not, or are not substantially, adversely affected by the addition(s) envisaged.

The compositions of the invention preferably comprise at least one surfactant.

The surfactants which are suitable for carrying out the present invention are in particular the following:

(i) Anionic Surfactant(s):

As examples of anionic surfactants which can be used, alone or as mixtures, in the context of the present invention, mention may be made in particular of salts (in particular alkali metal salts, especially sodium salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; ($C_6$–$C_{24}$)alkyl sulphosuccinates, ($C_6$–$C_{24}$)alkyl ether sulphosuccinates, ($C_6$–$C_{24}$)alkylamide sulphosuccinates; ($C_6$–$C_{24}$)alkyl sulphoacetates; ($C_6$–$C_{24}$)acyl sarcosinates and ($C_6$–$C_{24}$)acyl glutamates. It is also possible to use ($C_6$–$C_{24}$) alkylpolyglycoside carboxylic esters such as alkylglucoside citrates, alkylpolyglycoside tartrate and alkylpolyglycoside sulphosuccinates, alkyl sulphosuccinamates; acyl isethionates and N-acyltaurates, the alkyl or acyl radical of all these various compounds preferably comprising from 12 to 20 carbon atoms, and the aryl radical preferably denoting a phenyl or benzyl group. Among the anionic surfactants which can also be used, mention may also be made of fatty acid salts such as oleic, ricinoleic, palmitic and stearic acid salts, coconut oil acid or hydrogenated coconut oil acid; acyl lactylates in which the acyl radical comprises 8 to 20 carbon atoms. Alkyl D-galactosiduronic acids and salts thereof, polyoxyalkylenated ($C_6$–$C_{24}$)alkyl ether carboxylic acids, polyoxyalkylenated ($C_6$–$C_{24}$)alkylaryl ether carboxylic acids and polyoxyalkylenated ($C_6$–$C_{24}$)alkylamido ether carboxylic acids and salts thereof, in particular those comprising from 2 to 50 alkylene oxide groups, in particular ethylene oxide groups and mixtures thereof, can also be used.

(ii) Nonionic Surfactant(s):

The nonionic surfactants are, themselves also, compounds that are well known per se (see in particular in this respect "Handbook of Surfactants" by M. R. Porter, published by Blackie & Son (Glasgow and London), 1991, pp. 116–178), the disclosure of which is hereby incorporated by reference, and, in the context of the present invention, their nature is not a critical feature. Thus, they can be chosen in particular from polyethoxylated or polypropoxylated fatty acids, alkylphenols, α-diols or alcohols having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable in the context of the present invention.

(iii) Amphoteric or Zwitterionic Surfactant(s):

The amphoteric or zwitterionic surfactants, whose nature is not a critical feature in the context of the present invention, can be, in particular aliphatic secondary or tertiary amine derivatives in which the aliphatic radical is a linear or branched chain containing 8 to 18 carbon atoms and containing at least one water-soluble anionic group (for example carboxylate, sulphonate, sulphate, phosphate or phosphonate). Mention may also be made of ($C_8$–$C_{20}$) alkylbetaines, sulphobetaines, ($C_8$–$C_{20}$)alkylamido($C_1$–$C_6$) alkylbetaines or ($C_8$–$C_{20}$)alkylamido-($C_1$–$C_6$) alkylsulphobetaines.

Among the amine derivatives, mention may be made of the products described in U.S. Pat. Nos. 2,528,378 and 2,781,354 and classified in the CTFA dictionary, $3^{rd}$ edition, 1982, the disclosure of which is hereby incorporated by reference, under the names Amphocarboxyglycinates and Amphocarboxypropioniates, and having the respective structures:

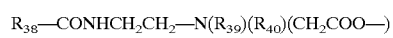

in which:

$R_{38}$ is an alkyl radical derived from an acid $R_{38}$—COOH present in hydrolyzed coconut oil, a heptyl, nonyl or undecyl radical;

$R_{39}$ is chosen form a β-hydroxyethyl group; and
$R_{40}$ is a carboxymethyl group; and $$R_{38}\text{—CONHCH}_2\text{CH}_2\text{—N(B)(C)}$$

in which:
B is —CH$_2$CH$_2$OX',
C is —(CH$_2$)$_z$—Y', with z=1 or 2,
X' is chosen from a —CH$_2$CH$_2$—COOH group or a hydrogen atom,
Y' is chosen from a —COOH or a —CH$_2$—CHOH—SO$_3$H radical,
$R_{38'}$ is an alkyl radical of an acid $R_{38'}$—COOH present in coconut oil or in hydrolyzed linseed oil, an alkyl radical, in particular a $C_7$, $C_9$, $C_{11}$ or $C_{13}$ alkyl radical, a $C_{17}$ alkyl radical and its iso form, an unsaturated $C_{17}$ radical.

These compounds are classified in the CTFA dictionary, 5th edition, 1993, the disclosure of which is hereby incorporated by reference, under the names disodium cocoamphodiacetate, disodium lauroamphodiacetate, disodium caprylamphodiacetate, disodium caproamphodiacetate, disodium cocoamphodipropionate, disodium lauroamphodipropionate, disodium caprylamphodipropionate, disodium caproamphodipropionate, lauroamphodipropionic acid, cocoamphodipropionic acid.

(iv) Cationic Surfactants:

Among the cationic surfactants which may be mentioned in particular are: optionally polyoxyalkylenated primary, secondary or tertiary fatty amine salts; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The amounts of surfactants present in the composition according to the invention can vary from 0.01 to 40% and preferably from 0.1 to 30% of the total weight of the composition.

The anhydrous bleaching composition can be in the form of a powder which produces a poultice after mixing with aqueous hydrogen peroxide solution. It can also be in the form of an anhydrous bleaching cream containing pulverulent agents suspended or dispersed in an organic solvent, such as the creams described in patents U.S. Pat. No. 4,170,637, DE 3 814 356, DE 3 844 956, EP 0 778 020 and DE 1 972 3538, the disclosures of all of which are hereby incorporated by reference.

According to the present invention, the anhydrous bleaching composition is preferably in the form of a powder of coated, uncoated or granulated particles.

A subject of the present invention is also a process for bleaching keratin fibers, in particular human hair.

This process comprises
mixing, immediately before use, the anhydrous bleaching composition containing at least one alkaline agent, at least one peroxygenated salt and the combination of at least one anionic and/or nonionic amphiphilic polymer comprising at least one fatty chain and at least one cationic or amphoteric substantive polymer with an aqueous hydrogen peroxide composition,
applying the mixture to the region of keratin fibers to be bleached,
leaving the mixture to stand on the fibers for a period which is sufficient to obtain the desired bleaching, this period generally ranging from 10 minutes to one hour, preferably ranging from 10 to 45 minutes, and
removing the bleaching mixture by rinsing with water, followed by washing with a shampoo, and then drying.

A further subject of the invention is the use of an anhydrous bleaching composition, as described above, to prepare a ready-to-use bleaching composition. For this, the anhydrous composition is mixed with about 0.5 to 10 equivalents by weight of an aqueous hydrogen peroxide composition, for example a solution, an emulsion or a gel with a weight concentration of from 2 to 12%. This mixing must be carried out immediately before applying the product to the hair.

The pH of the ready-to-use bleaching composition is preferably from 7 to 12 and even more preferably from 8.5 to 11.5.

Another subject of the invention is a packaging device in several parts, also known as a packaging "kit", comprising at least two compartments, one of which contains an anhydrous bleaching composition as described above, and the other of which contains an aqueous hydrogen peroxide composition.

The examples given below, purely by way of illustration and with no limiting nature, will allow the invention to be understood more clearly.

EXAMPLES 1 TO 3

The three bleaching compositions in pulverulent form, A, B and C below, were prepared:

| | Amounts (in % by weight) | | |
|---|---|---|---|
| | Composition A | Composition B | Composition C (invention) |
| Potassium persulphate | 35 | 35 | 35 |
| Sodium persulphate | 30 | 30 | 30 |
| Sodium metasilicate | 14 | 14 | 14 |
| Ammonium chloride | 5 | 5 | 5 |
| Ethylenediamine-tetraacetic acid | 1 | 1 | 1 |
| Sodiumdioctyl-sulphosuccinate/sodium benzoate | 1 | 1 | 1 |
| Calcium stearate | 1 | 1 | 1 |
| Silica | 9 | 8 | 6.5 |
| polyquaternium-22* | 0 | 1 | 1 |
| Crosslinked copolymer (acrylic acid/$C_{10-30}$ alkyl acrylate)** | 0 | 0 | 1.5 |
| Guar gum*** | 2 | 2 | 2 |
| Hydroxyethyl-cellulose | 2 | 2 | 2 |

*MERQUAT 280 dry sold by the company Calgon
**CARBOPOL 1382 sold by the company Goodrich
***sold under the name GUARGEL D/15 by the company Société Francaise des Colloïdes The hydrogen peroxide composition D below was also prepared:

| | Composition D (amount in % by weight) |
|---|---|
| Cetearyl alcohol/ceteareth-30 | 2.85 |
| Stabilizers | 0.06 |
| Sequestering agent | 0.15 |
| Hydrogen peroxide | 9 |
| Phosphoric acid | qs pH 2 |
| Distilled water | qs 100 |

8 g of each of the bleaching compositions A, B and C were mixed with 16 g of the hydrogen peroxide composition D.

Three successive bleaching cycles were carried out on 3 g locks of chestnut-coloured hair using each of the ready-to-use compositions AD, BD and CD, according to the following protocol:

A lock of hair was immersed in each of the ready-to-use compositions, after starting the timer, and the lock was then spread out in a fan shape on a plate thermostatically maintained at 31° C. The fanned-out lock was coated with half of the mixture and was left to stand for 20 minutes. After 20 minutes, the lock was quickly turned over and coated with the rest of the mixture, then left to stand for a further 20 minutes. At the end of the exposure time, the lock was rinsed thoroughly with water until the water was clear. A neutralizing shampoo-wash was carried out in order to remove any traces of oxidizing agent. The lock was disentangled with a comb and dried for 1 hour with an electric dryer at 60° C., while protecting it with a paper towel. The lock was once again moistened and washed again with standard shampoo. It was disentangled and then dried again for 1 hour with an electric dryer at 60° C.

After bleaching, each 3 g lock was divided into 5 locks of 0.6 g, each of these locks being subjected to the alkaline solubility test described below.

Each of the 5 locks was placed in a crystallizing dish which was put in an oven at 60° C. for 30 minutes; the crystallizing dishes containing the locks were weighed after heating them in an oven ($P_0$). The locks were removed from the crystallizing dishes and these empty dishes were weighed ($P_1$). Next, the locks were put back into the crystallizing dishes and these dishes were placed in a desiccator for 24 hours.

40 ml of NaOH (0.1 N) solution were introduced into 50 ml conical flasks and the flasks were placed on a waterbath thermostatically maintained at 65° C. When the temperature was stabilized, the locks of hair to be tested were immersed for 30 minutes in the alkaline solution, stirring cautiously 2 to 3 times. The locks of hair were removed and a series of three washes was then carried out, each wash comprising immersing the lock for 15 minutes in 100 ml of demineralized water while stirring gently from time to time. The locks thus rinsed were then left to drip-dry and were placed in the pre-tared crystallizing dishes ($P_1$). The crystallizing dish+lock assembly was placed in an oven and dried for 24 hours at 105° C. After cooling for 45 minutes in a desiccator, the crystallizing dishes containing the locks were weighed again ($P_2$).

The alkaline solubility (AS), measuring the weight loss of the lock, expressed in %, was calculated in the following way:

$$AS=(P_0-P_2)/(P_0-P_1-a)\times 100$$

in which ($P_0-P_2$) represents the weight loss of the lock during the test and ($P_0-P_1-a$) represents the initial weight of the lock, a corresponding to the weight of the lock attachment (0.07 g).

Measurement of the alkaline solubility of the hair makes it possible to take account of the degradation of the keratin fibers resulting from their bleaching. Specifically, oxidation of the disulphide bridges of keratin into sulphonic acid groups during the bleaching increases the solubility of the treated hair in an alkaline solution. The higher the alkaline solubility, the greater the degradation of the fiber.

The results of these alkaline solubility tests summarized in the table below are the average values calculated from the results for 5 individual locks.

| | Alkaline solubility (in %) | |
|---|---|---|
| | Average | Standard deviation |
| Composition AD | 54.5 | 3.1 |
| Composition BD | 54.6 | 2.1 |
| Composition CD (invention) | 45.4 | 2.4 |

These results show that the use of the amphoteric substantive polymer (Polyquaternium-22) alone (composition BD) does not make it possible to limit the degradation of the fiber when compared with the composition containing neither substantive polymer nor amphiphilic polymer (composition AD).

On the other hand, the combination according to the invention of an anionic amphiphilic copolymer of acrylic acid and of ($C_{10}$–$C_{30}$) alkyl acrylate (CARBOPOL1382 from the company Goodrich) with the amphoteric substantive polymer Polyquaternium-22 (composition CD) significantly reduces the alkaline solubility of the bleached keratin fibers.

EXAMPLE 4

The bleaching composition in pulverulent form, E, below was prepared (amounts in % by weight)

| | |
|---|---|
| Potassium persulphate | 38 |
| Sodium persulphate | 30 |
| Sodium metasilicate | 14 |
| Ammonium chloride | 5 |
| Ethylenediamine tetraacetic acid | 1 |
| Sodium dioctylsulphosuccinate/ sodium benzoate | 2 |
| Silica | 2 |
| Polyquaternium-22 | 1 |
| Cetylhydroxyethylcellulose sold under the name POLYSURF 67 by the company Hercules | 4 |

8 g of this composition E were mixed with 16 g of composition D described above. This mixture was applied and maintained on hair to be bleached, for 45 minutes. After rinsing, shampooing and drying, a uniform bleaching effect was obtained. The state of the fiber was satisfactory, with limited degradation.

EXAMPLE 5

The bleaching composition in the form of an anhydrous cream, F, below was prepared (amounts in % by weight):

| | |
|---|---|
| Isopropyl palmitate | 23 |
| Mineral oil | 3 |
| Potassium persulphate | 27 |
| Sodium persulphate | 20 |
| Sodium metasilicate | 12 |
| Ammonium chloride | 4 |
| Ethylenediaminetetraacetic acid | 1 |
| Cetylstearyl alcohol containing 25 mol of ethylene oxide | 2 |
| Clay | 1 |
| Polyquaternium-22 | 1 |
| SERAD FX-1100 | 3 |
| Titanium oxide | 1 |
| Magnesium stearate | 2 |

10 g of this composition F were mixed with 15 g of composition D described above. This mixture was applied to and maintained on hair to be bleached, for 45 minutes. After rinsing, shampooing and drying, a uniform bleaching effect was obtained. The state of the fiber was satisfactory, with limited degradation.

The foregoing written description relates to various embodiments of the present invention. Numerous changes and modifications may be made therein without departing from the spirit and scope of the invention as defined in the following claims.

What is claimed is:

1. An anhydrous composition for bleaching keratin fibers comprising:

at least one alkaline agent, at least one peroxygenated salt, at least one amphiphilic polymer chosen from nonionic and anionic amphiphilic polymers and comprising at least one fatty chain, and at least one substantive polymer chosen from cationic and amphoteric substantive polymers.

2. The composition according to claim 1, wherein the keratin fibers are human keratin fibers.

3. The composition according to claim 1, wherein the at least one anionic amphiphilic polymer comprising at least one fatty chain is a copolymer comprising hydrophilic units derived from one or more monomers containing ethylenic unsaturation and bearing a carboxylic acid function, and hydrophobic units derived from one or more monomers containing ethylenic unsaturation and bearing a hydrophobic side chain.

4. The composition according to claim 3, wherein the monomers containing ethylenic unsaturation and bearing a carboxylic acid function are chosen from ethacrylic acid, methacrylic acid and acrylic acid, and mixtures thereof.

5. The composition according to claim 3, wherein the monomers containing ethylenic unsaturation and bearing a carboxylic acid function are chosen from methacrylic acid and acrylic acid.

6. The composition according to claim 3, wherein the monomers containing ethylenic unsaturation and bearing a hydrophobic side chain are chosen from $(C_{10}-C_{30})$, alkyl ethacrylates, methacrylates and acrylates.

7. The composition according to claim 3, wherein the monomers containing ethylenic unsaturation and bearing a hydrophobic side chain are chosen from $(C_{12}-C_{22})$, alkyl ethacrylates, methacrylates and acrylates.

8. The composition according to claim 3, wherein the monomers containing ethylenic unsaturation and bearing a hydrophobic side chain are chosen from allyl fatty alkyl ethers corresponding to the formula $$CH_2=CR'CH_2-O-B_n-R \qquad (I)$$

in which

R' is chosen from a hydrogen atom and a methyl group,

B is an ethylenoxy group, n is an integer ranging from 0 to 100,

R is a hydrocarbon-based group chosen from alkyl, arylalkyl, aryl, alkylaryl and cycloalkyl residues comprising from 8 to 30 carbon atoms.

9. The composition according to claim 8, wherein R is a hydrocarbon-based group chosen from alkyl, arylalkyl, aryl, alkylaryl and cycloalkyl residues comprising from 10 to 24 carbon atoms.

10. The composition according to claim 1, wherein the at least one anionic amphiphilic polymer comprising at least one fatty chain also comprises units derived from a crosslinking monomer containing two non-conjugated ethylenic double bonds.

11. The composition according to claim 10, wherein the crosslinking monomer is chosen from diallyl phthalate, allyl (meth)acrylate, divinylbenzene, (poly)ethylene glycol dimethacrylate, methylenebisacrylamide, polyallylsucrose or polyallylpentaerythritol.

12. The composition according to claim 1, wherein the at least one anionic amphiphilic polymer comprising at least one fatty chain is a crosslinked copolymer of acrylic acid and of $C_{10}-C_{30}$ alkyl acrylate.

13. The composition according to claim 1, wherein the at least one nonionic amphiphilic polymer comprising at least one fatty chain is chosen from celluloses or hydroxyalkylcelluloses modified with groups comprising at least one fatty chain of alkyl, arylalkyl or alkylaryl type containing a $(C_8-C_{22})$ alkyl group, or with polyalkoxylated alkylphenol groups;

hydroxypropyl guars modified with groups comprising at least one $(C_8-C_{22})$ fatty chain;

polyurethanes comprising at least one fatty chain of $(C_8-C_{30})$ alkyl or alkenyl type;

copolymers of vinylpyrrolidone and of hydrophobic monomers containing a fatty chain;

copolymers of $(C_1-C_6)$ alkyl (meth)acrylates and of amphiphilic monomers comprising at least one fatty chain; and copolymers of hydrophilic (meth)acrylates and of hydrophobic monomers comprising at least one fatty chain.

14. The composition according to claim 13, wherein the at least one nonionic amphiphilic polymer comprising at least one fatty chain is a hydroxyethylcellulose modified with groups comprising at least one $(C_8-C_{22})$ alkyl group or a polyurethane modified with at least one $(C_{10}-C_{20})$ alkyl chain.

15. The composition according to claim 1, wherein the at least one amphiphilic polymer is present in the composition in an amount ranging from 0.03 to 30% by weight relative to the total weight of the composition.

16. The composition according to claim 15, wherein the at least one amphiphilic polymer is present in the composition in an amount ranging from 0.3 to 15% by weight relative to the total weight of the composition.

17. The composition according to claim 1, wherein the at least one substantive polymer chosen from cationic and amphoteric substantive polymers is a polymer containing units comprising amine groups chosen from primary, secondary, tertiary and quaternary amine groups which can either form part of the main chain of the polymer or can be borne by a side substituent which is directly connected thereto, said polymer having a number-average molecular mass ranging from 500 to 5,000,000.

18. The composition according to claim 17, wherein the at least one substantive polymer has a number-average molecular mass ranging from 1000 to 3,000,000.

19. The composition according to claim 17, wherein said at least one substantive polymer is chosen from quaternized cellulose derivatives and polyacrylates containing quaternized or non-quaternized amino side groups.

20. The composition according to claim 19, wherein the quaternized cellulose derivatives are chosen from quaternized celluloses modified with groups comprising at least one fatty chain, chosen from alkyl, arylalkyl and alkylaryl groups comprising at least 8 carbon atoms, or mixtures thereof, and quaternized hydroxyethylcelluloses modified with groups comprising at least one fatty chain, chosen from alkyl, arylalkyl and alkylaryl groups comprising at least 8 carbon atoms, or mixtures thereof.

21. The composition according to claim 17, wherein the at least one cationic substantive polymer is a dimethyldiallylammonium chloride homopolymer or a copolymer of dimethyldiallylammonium and of acrylamide.

22. The composition according to claim 17, wherein the at least one cationic substantive polymer is a poly (quaternary ammonium) comprising repeating units corresponding to a formula chosen from the formula (XXI):

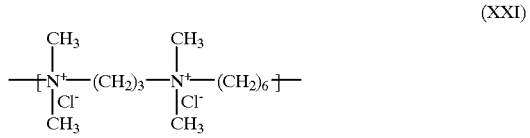

the formula (XXII):

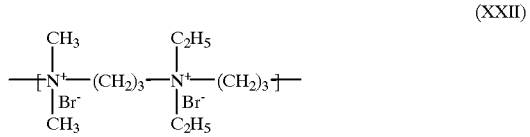

and the formula (XXIII):

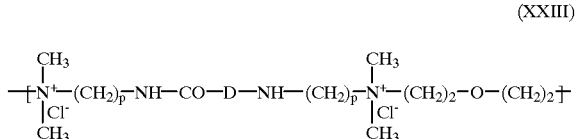

in which:
p is an integer ranging from 1 to 6, and
D is chosen from a single bond and a group —$(CH_2)_r$— CO— in which r is 4 or 7.

23. The composition according to claim 17, wherein the at least one amphoteric substantive polymer is chosen from Polyquaternium-22, Polyquaternium-39 and Polyquaternium47.

24. The composition according to claim 1, wherein the at least one substantive polymer is present in the composition in an amount ranging from 0.03 to 30% by weight relative to the total weight of the composition.

25. The composition according to claim 24, wherein the at least one substantive polymer is present in the composition in an amount ranging from 0.3 to 15% by weight relative to the total weight of the composition.

26. The composition according to claim 1, wherein the at least one amphiphilic polymer and the at least one substantive polymer are present in said composition in a weight ratio ranging from 10:1 to 1:10.

27. The composition according to claim 26, wherein the at least one amphiphilic polymer and the at least one substantive polymer are present in said composition in a weight ratio ranging from 5:1 to 1:5.

28. The composition according to claim 1, wherein the at least one alkaline agent is chosen from ammonium salts, and alkali metal or alkaline-earth metal silicates, phosphates or carbonates.

29. The composition according to claim 28, wherein the ammonium salts are chosen from ammonium chloride, sulphate, phosphate and nitrate.

30. The composition according to claim 28, wherein the at least one alkaline agent is an alkali metal metasilicate.

31. The composition according to claim 1, wherein the at least one peroxygenated salt is chosen from the ammonium and alkali metal persulphates, percarbonates and perborates.

32. The composition according to claim 1, wherein the at least one peroxygenated salt is chosen from sodium persulphate and potassium persulphate.

33. The composition according to claim 1, wherein the at least one peroxygenated salt is present in the composition in an amount ranging from 20 to 70% by weight calculated relative to the total weight of the composition.

34. The composition according to claim 33, wherein the at least one peroxygenated salt is present in the composition in an amount ranging from 30 to 60% by weight calculated relative to the total weight of the composition.

35. The composition according to claim 1, wherein the composition further comprises bleaching adjuvants chosen from agents for controlling the release of oxygen, thickening or gelling polymers, anionic, nonionic, cationic, amphoteric or zwitterionic surfactants and mixtures thereof, mineral or plant oils, waxes, granulating adjuvants, binders, mineral fillers, opacifiers, dyes, sequestering agents and fragrances.

36. The composition according to claim 35, wherein the opacifier is titanium oxide.

37. The composition according to claim 35, wherein the composition comprises from 0.01 to 40% by weight of at least one surfactant.

38. The composition according to claim 37, wherein the composition further comprises from 0.1 to 30% by weight of at least one surfactant.

39. The composition according claim 1, wherein the composition is in the form of a powder, or of a suspension or dispersion of powder in an anhydrous organic liquid support.

40. The composition according to claim 1, further comprising a medium suitable for bleaching.

41. A process for bleaching keratin fibers comprising:
mixing, immediately before application an anhydrous bleaching composition comprising at least one alkaline agent, at least one peroxygenated salt, at least one amphiphilic polymer chosen from nonionic and anionic amphiphilic polymers and comprising at least one fatty chain, and at least one substantive polymer chosen from cationic and amphoteric substantive polymers, with an aqueous hydrogen peroxide composition,
applying the mixture obtained to the keratin fibers to be bleached,
leaving the mixture to stand on the fibers for a period which is sufficient to obtain the desired bleaching effect, and
removing the bleaching mixture by rinsing with water, followed by washing with a shampoo, and then drying.

42. The process according to claim 41, wherein said anhydrous bleaching composition comprises a medium suitable for bleaching.

43. A multi-compartment device for bleaching keratin fibers, comprising a first compartment and a second compartment wherein said first compartment contains an anhydrous composition comprising at least one alkaline agent, at least one peroxygenated salt, at least one amphiphilic polymer chosen from nonionic and anionic amphiphilic polymers and comprising at least one fatty chain, and at least one substantive polymer chosen from cationic and amphoteric substantive polymers, and
the second compartment contains an aqueous hydrogen peroxide composition.

44. The device according to claim 43, wherein the keratin fibers are human keratin fibers.

45. The device according to claim 44, wherein the human keratin fibers are hair.

46. A ready-to-use bleaching composition comprising an aqueous hydrogen peroxide composition and an anhydrous composition comprising at least one alkaline agent, at least one peroxygenated salt, at least one amphiphilic polymer chosen from nonionic and anionic amphiphilic polymers and comprising at least one fatty chain, and at least one substantive polymer chosen from cationic and amphoteric substantive polymers.

47. The composition according to claim 46, wherein said aqueous hydrogen peroxide composition is present in said bleaching composition in an amount ranging from 0.5 to 10 equivalents by weight of said anhydrous composition.

* * * * *